United States Patent
Teitelbaum

(10) Patent No.: US 11,260,203 B2
(45) Date of Patent: Mar. 1, 2022

(54) ANCHOR DEVICE FOR USE WITH CATHETERS

(71) Applicant: ANCHOR ENDOVASCULAR, INC., Fremont, CA (US)

(72) Inventor: George P. Teitelbaum, Santa Monica, CA (US)

(73) Assignee: ANCHOR ENDOVASCULAR, INC., Fremont, CA (US)

( * ) Notice: Subject to any disclaimer, the term of this patent is extended or adjusted under 35 U.S.C. 154(b) by 352 days.

(21) Appl. No.: 16/443,578

(22) Filed: Jun. 17, 2019

(65) Prior Publication Data

US 2019/0298972 A1    Oct. 3, 2019

Related U.S. Application Data

(60) Continuation of application No. 15/593,175, filed on May 11, 2017, now Pat. No. 10,322,263, which is a
(Continued)

(51) Int. Cl.
*A61F 2/95*    (2013.01)
*A61M 25/04*    (2006.01)
(Continued)

(52) U.S. Cl.
CPC ....... *A61M 25/04* (2013.01); *A61B 17/12186* (2013.01); *A61F 2/013* (2013.01);
(Continued)

(58) Field of Classification Search
CPC ...... A61F 2/01; A61F 2/90; A61F 2/95; A61F 2/07; A61F 2/954; A61F 2/958;
(Continued)

(56) References Cited

U.S. PATENT DOCUMENTS

| | | |
|---|---|---|
| 5,256,146 A | 10/1993 | Ensminger et al. |
| 5,405,380 A | 4/1995 | Gianotti |

(Continued)

FOREIGN PATENT DOCUMENTS

| | | |
|---|---|---|
| EP | 1054635 B1 | 1/2010 |
| WO | 1991007928 A1 | 6/1991 |

(Continued)

OTHER PUBLICATIONS

U.S. Appl. No. 14/959,847, Non-Final Office Action, dated Feb. 27, 2017, 10 pages.

(Continued)

*Primary Examiner* — Vi X Nguyen
(74) *Attorney, Agent, or Firm* — Stoel Rives LLP

(57) ABSTRACT

An anchor device to simplify catheterization procedures, particularly for insertion and maneuvering of large catheters in tortuous arteries, vessels, or other lumen is disclosed. In some embodiments, the anchor device includes an anchor stent formed from a plurality of zig-zag shaped wire elements that are coupled together. The device further includes a plurality of connector struts attached at a proximal end of the anchor stent, the connector struts coalescing to form a strut tip. A guide device, such as a guidewire, is attached to the anchor stent at the strut tip and may be used to guide the anchor stent into the arteries or other vessels and toward a target treatment site.

12 Claims, 3 Drawing Sheets

Related U.S. Application Data division of application No. 15/403,442, filed on Jan. 11, 2017, now Pat. No. 9,656,047, which is a continuation of application No. 14/959,847, filed on Dec. 4, 2015, now Pat. No. 9,682,216.

(60) Provisional application No. 62/088,382, filed on Dec. 5, 2014.

(51) Int. Cl.
| | |
|---|---|
| *A61M 25/09* | (2006.01) |
| *A61M 25/01* | (2006.01) |
| *A61F 2/01* | (2006.01) |
| *A61B 17/12* | (2006.01) |
| *A61F 2/90* | (2013.01) |
| *A61M 25/00* | (2006.01) |

(52) U.S. Cl.
CPC .............. *A61F 2/90* (2013.01); *A61M 25/01* (2013.01); *A61M 25/0108* (2013.01); *A61M 25/09* (2013.01); *A61F 2/95* (2013.01); *A61F 2002/016* (2013.01); *A61M 2025/0042* (2013.01); *A61M 2025/09183* (2013.01)

(58) Field of Classification Search
CPC ....... A61F 2/966; A61M 25/04; A61M 25/01; A61M 25/09; A61M 25/0108
See application file for complete search history.

(56) References Cited

U.S. PATENT DOCUMENTS

| | | | |
|---|---|---|---|
| 5,509,900 | A | 4/1996 | Kirkman |
| 5,607,466 | A | 3/1997 | Imbert et al. |
| 5,792,156 | A | 8/1998 | Perouse |
| 6,033,413 | A | 3/2000 | Mikus et al. |
| 6,074,378 | A | 6/2000 | Mouri et al. |
| 7,753,906 | B2 | 7/2010 | Esposito |
| 8,019,438 | B2 | 9/2011 | Johnson et al. |
| 8,388,680 | B2 | 3/2013 | Starksen et al. |
| 8,764,725 | B2 | 7/2014 | Averbuch |
| 9,108,925 | B2 | 8/2015 | Bonrath et al. |
| 9,126,016 | B2 | 9/2015 | Fulton |
| 9,682,216 | B2 | 6/2017 | Teitelbaum |
| 2003/0191492 | A1 | 10/2003 | Gellman et al. |
| 2003/0236533 | A1* | 12/2003 | Wilson ............ A61B 17/22031 606/127 |
| 2004/0254597 | A1 | 12/2004 | Schwartz et al. |
| 2005/0228417 | A1* | 10/2005 | Teitelbaum ...... A61B 17/22031 606/159 |
| 2005/0273147 | A1 | 12/2005 | Israel |
| 2006/0089704 | A1 | 4/2006 | Douglas |
| 2006/0259063 | A1 | 11/2006 | Bates et al. |
| 2007/0123925 | A1 | 5/2007 | Thierry et al. |
| 2008/0045863 | A1 | 2/2008 | Bakos |
| 2008/0125760 | A1 | 5/2008 | Gilboa |
| 2009/0171293 | A1 | 7/2009 | Yang et al. |
| 2010/0268029 | A1 | 10/2010 | Phan et al. |
| 2010/0274223 | A1 | 10/2010 | Teitelbaum et al. |
| 2010/0318172 | A1 | 12/2010 | Schaefer |
| 2011/0276047 | A1 | 11/2011 | Sklar et al. |
| 2012/0022579 | A1 | 1/2012 | Fulton |
| 2012/0101560 | A1 | 4/2012 | Kluck |
| 2012/0172844 | A1 | 7/2012 | Mullen |
| 2013/0281788 | A1 | 10/2013 | Garrison |
| 2014/0180166 | A1 | 6/2014 | Isch |
| 2015/0005763 | A1 | 1/2015 | Klink |
| 2015/0073526 | A1 | 3/2015 | Kluck |
| 2016/0101267 | A1 | 4/2016 | Kelly |
| 2016/0199617 | A1 | 7/2016 | Pigott |
| 2017/0246426 | A1 | 8/2017 | Teitelbaum |

FOREIGN PATENT DOCUMENTS

| | | |
|---|---|---|
| WO | 2010119445 A1 | 10/2010 |
| WO | 2014165754 A1 | 10/2014 |
| WO | 2015123671 A3 | 8/2015 |

OTHER PUBLICATIONS

U.S. Appl. No. 14/959,847, Notice of Allowance, dated May 10, 2017, 8 pages.

U.S. Appl. No. 15/403,442, Notice of Allowance, dated Apr. 14, 2017, 11 pages.

U.S. Appl. No. 15/403,442, Non-Final Office Action, dated Feb. 27, 2017, 18 pages.

U.S. Appl. No. 15/593,175, Notice of Allowance, dated Feb. 7, 2019, 9 pages.

U.S. Appl. No. 15/593,175, Non-Final Office Action, dated Nov. 29, 2018, 11 pages.

* cited by examiner

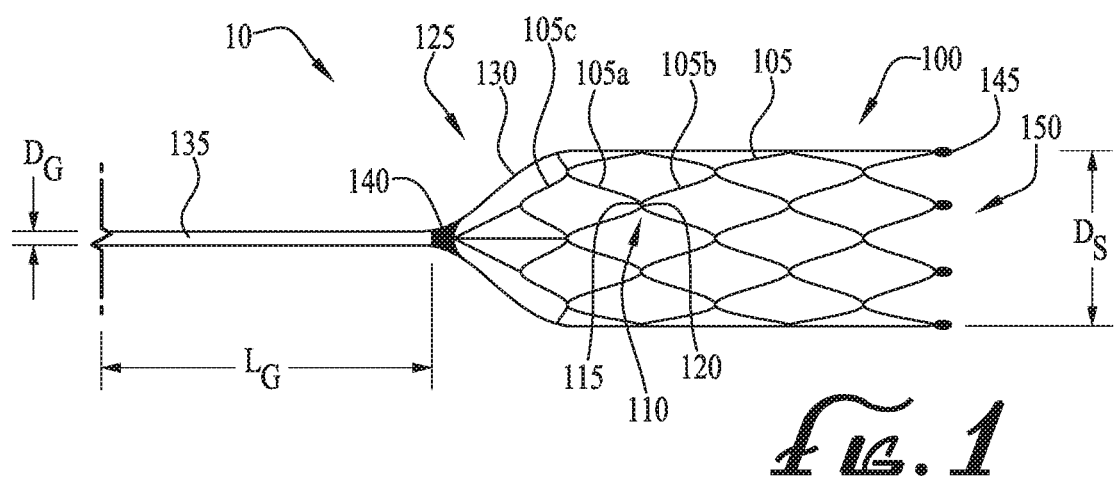
fig.1
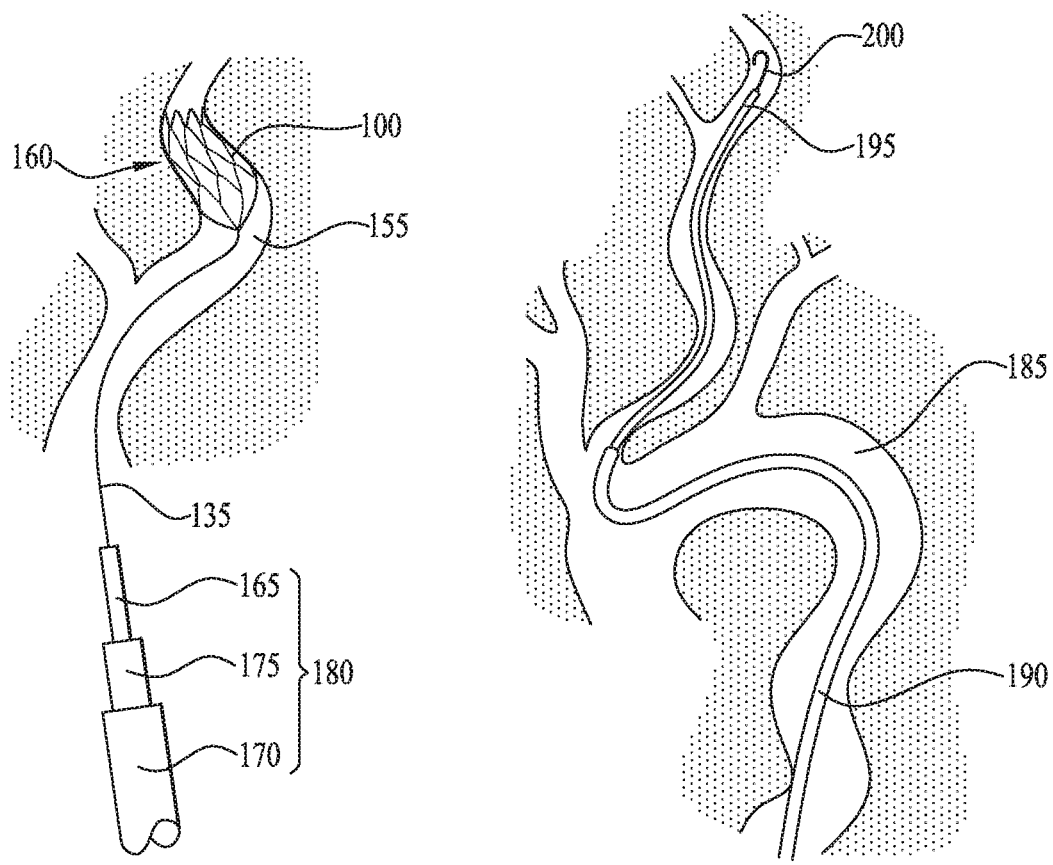
fig.2
fig.3

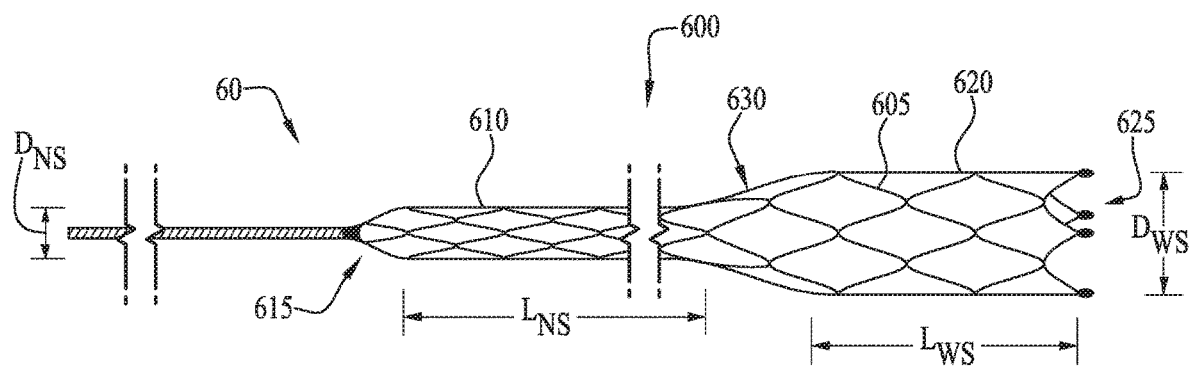
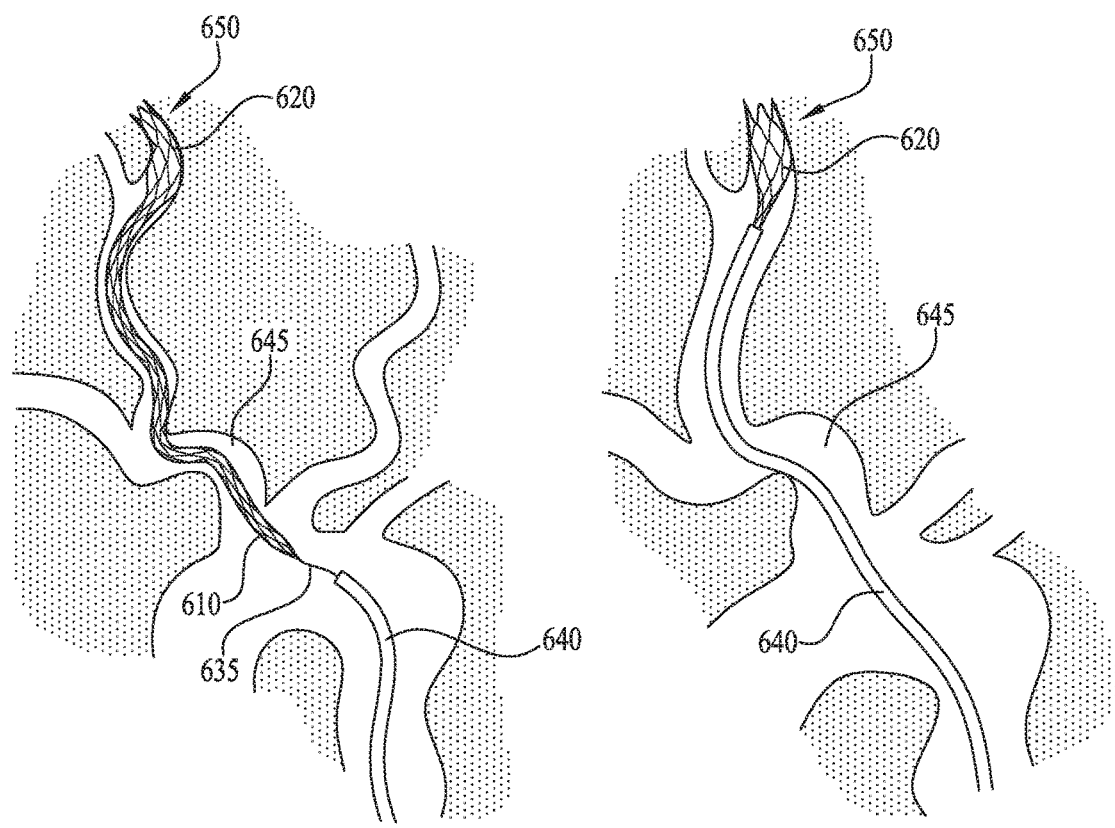

ANCHOR DEVICE FOR USE WITH CATHETERS

RELATED APPLICATION DATA

This application is a continuation of U.S. patent application Ser. No. 15/593,175, filed May 11, 2017, which is a divisional of U.S. patent application Ser. No. 15/403,442, filed Jan. 11, 2017, which is a continuation of U.S. patent application Ser. No. 14/959,847, filed Dec. 4, 2015, which claims the benefit under 35 U.S.C. § 119(e) of U.S. Provisional Patent Application No. 62/088,382, filed Dec. 5, 2014, each of which is hereby incorporated by reference herein in its entirety.

TECHNICAL FIELD

The field of the present disclosure relates generally to medical devices, and in particular, to anchor devices that may be used to advance large catheters within tortuous vascular or non-vascular anatomy.

BACKGROUND

In the medical industry, it is customary to use catheters that extend into arteries, vessels, or other lumen of a patient's body to introduce or remove liquids, particles, or other substances into or out of the patient's body, or to support other suitable treatment procedures. Controlled placement of catheters is important in many facets of the medical field. For example, drug delivery catheters provide a means for delivering concentrated drugs or other substances to a specific site to maximize the therapeutic effect, while minimizing side effects that may occur from receiving drugs orally or intravenously.

In some procedures, it may be necessary to advance a large catheter within tortuous vascular and non-vascular tubular anatomy to reach a target site. Typically, such procedures may require medical personnel to impart greater force to maneuver the catheter within the tortuous vessel. In such procedures, it is important to gauge the insertion force of the catheter properly to avoid inserting the catheter farther than anticipated, which may lead to unintended complications or may make it difficult to provide treatment to the target site. In addition, it is also important that catheters are firmly secured once positioned in the lumen, and that the catheters remain in the desired position despite the patient's movement or other factors that may disturb the position of the catheter to avoid causing potential trauma by the unexpected removal of the catheter.

BRIEF DESCRIPTION OF THE DRAWINGS

FIG. 1 illustrates an example anchor device according to one embodiment.

FIGS. 2 and 3 illustrate an example use of a multi-axial catheter system with the anchor device of FIG. 1 according to one embodiment.

FIG. 6 illustrates an example of an anchor device with an anchor stent having varying thickness profiles in accordance with one embodiment.

FIGS. 7 and 8 illustrate an example use of a catheter with the anchor device of FIG. 6 in accordance with one embodiment.

DETAILED DESCRIPTION OF EXAMPLE EMBODIMENTS

Figure 4:
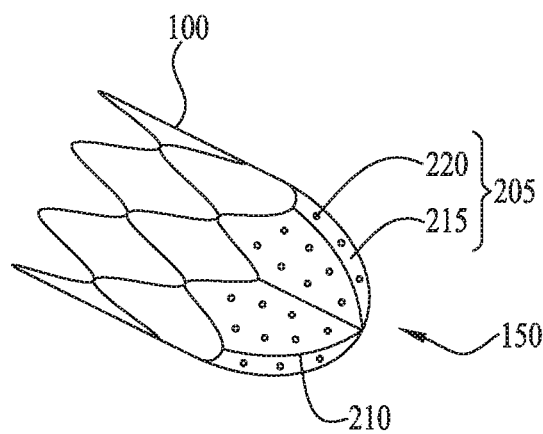
FIG. 4 illustrates an embodiment of an anchor stent with a distal end fitted with a porous barrier.

With reference to the drawings, this section describes particular embodiments and their detailed construction and operation. The embodiments described herein are set forth by way of illustration only and not limitation. The described features, structures, characteristics, and methods of operation may be combined in any suitable manner in one or more embodiments. In view of the disclosure herein, those skilled in the art will recognize that the various embodiments can be practiced without one or more of the specific details or with other methods, components, materials, or the like. For the sake of clarity and conciseness, certain aspects of components or steps of certain embodiments are presented without undue detail where such detail would be apparent to those skilled in the art in light of the teachings herein and/or where such detail would obfuscate an understanding of more pertinent aspects of the embodiments.

The present inventor has recognized a need for an anchor device having an improved design to simplify catheterization procedures. As is further described below, certain embodiments disclosed herein may be capable of achieving various advantages, including one or more of the following: (1) providing an anchor device with a streamlined design to simplify endovascular introduction and decrease forces required to position delivery catheters at desired sites; (2) providing such an anchor device suitable to aid in advancing large catheters within tortuous vascular (and non-vascular tubular) anatomy; and (3) providing such an anchor device capable of securing the catheter in position to minimize the risk of dislodgment. Additional aspects and advantages will be apparent from the following detailed description of example embodiments, which proceeds with reference to the accompanying drawings.

Collectively, FIGS. 1-8 illustrate various embodiments of an anchor device 10, 50, 60 that may be employed endovascularly and used in conjunction with delivery catheters for a variety of medical procedures, such as for stroke thrombectomy or drug delivery purposes. With general reference to FIG. 1, the anchor device 10 is a generally tubular device including an anchor stent 100 formed of a plurality of wire elements 105, where each individual wire element 105 is shaped in a zig-zag pattern and coupled to adjacent wire elements. As is further described with reference to FIGS. 1-3, the anchor device 10 may be used as a means to provide a distal anchor point for a guide wire 135 to aid in the advancement of large catheters within tortuous vascular (and non-vascular tubular) anatomy 155.

In other embodiments, the anchor device 10, or a miniaturized version thereof, may be used to allow intracranial catheter exchanges with greater stability and much lower risk of vessel perforations. In another embodiment, the anchor device 10, or a larger version thereof, may be useful for catheter exchanges in large vessels like the aorta or pulmonary arteries, such as during aortic aneurysm stent-graft insertions. In still other embodiments, the anchor device 10 may be useful in non-vascular catheter interventions, such as in the biliary tree, ureters, and tracheobronchial tree, or may be useful as an anchor-filter or as an access aid during carotid stenting, or may be useful as an embolic device. Additional details of these and other embodiments are further described in detail below with reference to the figures.

With particular reference to FIG. 1, the following sections describe additional details of the anchor device 10 and the components thereof. As briefly described previously, the anchor device 10 includes a plurality of wire elements 105 coupled together to form an anchor stent 100, which is a generally tubular-shaped, self-expanding mesh structure. In some embodiments, the wire elements 105 may be coupled together, such as via a welding process, to create a "closed-cell" design with sufficient rigidity to allow the anchor stent 100 to move through tortuous vessel 155 (see FIGS. 2 and 3). For example, with general reference to FIG. 1, adjoining wire elements 105a and 105b may be welded at every junction 110 where respective ends 115, 120 of the adjoining wire elements 105a, 105b meet. In this configuration, the anchor stent 100 is afforded sufficient rigidity to move through the tortuous vessel 155 as further described below with reference to FIGS. 2-3. The diameter of the anchor stent 100 may vary depending upon the size of the vessel or tubular body structure in which the anchor device 10 is to be used. In various embodiments, the anchor stent 100 may be provided in a variety of fully expanded diameters ranging from 2 mm up to 30 mm. In other embodiments, the anchor stent 100 may be larger than 30 mm.

As described previously, the anchor stent 100 may have a "closed-cell" design. However, in other embodiments, the anchor stent 100 may instead have a more "open-cell" design so that the anchor stent 100 is capable of following sharp curves without kinking. For example, in one embodiment, the adjoining wire elements 105a, 105b may instead be welded at alternating junctions, thereby creating an anchor stent 100 with some welded ends, but leaving some ends not welded or otherwise attached to one another. In this configuration, the staggered welds between the adjacent wire elements 105a, 105b may help impart greater flexibility to the anchor stent 100 without sacrificing overall stability.

In some embodiments, the wire elements 105 may be composed of a metallic material exhibiting shape memory/superelasticity qualities, such as nitinol (a nickel-titanium alloy), Elgiloy (a cobalt, chromium, and nickel based alloy) or other suitable shape-memory alloys. Alternatively, in other embodiments, the wire elements 105 may be composed of other suitable materials, including non-metallic materials, capable of creating the tubular stent structure. In still other embodiments, the wire elements 105 may be composed of a stiffer metallic material to provide greater rigidity and stiffness to the anchor device 100. Depending on the requirements of the clinical situation and/or other factors, the anchor stent 100 may be made of different materials to provide suitable degrees of stiffness as may be necessary.

With reference to FIG. 1, a proximal end 125 of the anchor stent 100 includes a plurality of connector struts 130 affixed to an outermost wire element 105c on one end, and permanently affixed (such as via a weld or other securement means) to a proximal guidewire 135 at an attachment zone 140 at an opposite end. The proximal guidewire 135 may be formed with any one of a variety of diameters that may range from 0.008 in. to 0.040 in., and may be provided in any one of a variety of lengths that may range from 90 cm to 350 cm. In use, the anchor stent 100 provides a means to secure in place the distal end of the guidewire 135 to aid in advancing large bore catheters to their intended target site distally within tortuous blood vessels and other non-vascular tubular anatomy as further described with reference to FIGS. 2 and 3.

As illustrated in FIG. 1, the anchor stent 100 may include radiopaque markers 145 at a distal end 150 thereof. Using fluoroscopy, the radiopaque markers 145 allow an operator to view a position of the anchor stent 100 and to determine whether the anchor stent 100 has reached a desired treatment site and properly engaged the interior wall of the blood vessels or other lumen. In other embodiments, the wire elements 105 may also (or alternatively) include radiopaque material so that the periphery/boundary of the stent frame may be viewed.

As mentioned previously, FIGS. 2 and 3 illustrate example embodiments for employing the anchor device 10 to guide a catheter through tortuous vessels 155. With reference to FIGS. 2 and 3, the following describes one configuration of the anchor device 10 that may be well-suited for use in tortuous vessels 155, such as cervical carotid and vertebral arteries. In this configuration, to help ensure that the anchor device 10 is able to travel through the tortuous vessel 155 to a target site 160, the diameter $D_G$ of the proximal guidewire 135 may range from between 0.010" to 0.018," and have a length $L_G$ ranging from between 260 cm to 300 cm, and the anchor stent 100 may have a diameter $D_S$ ranging between 5 mm to 8 mm. It should be understood that these example ranges are for illustration purposes only and may be different depending on the characteristics of the vessel or lumen with which the anchor device 10 is being employed.

With particular reference to FIG. 2, the anchor stent 100 is introduced and advanced into the target artery 155 via the guidewire 135. The anchor stent 100 may be introduced (and subsequently retrieved as described below) through a microcatheter 165. In some embodiments, the microcatheter 165 may have a size 2.3-F to 2.8-F microcatheter, with an inner diameter ranging between 0.021 in. and 0.027 in. The stiffness of both the guidewire 135 and the anchor stent 100 help ensure that the anchor stent 100 travels through the artery 155 and to the target site 160 with relative ease. Once the anchor stent 100 reaches the target site 160, the anchor stent 100 is in a fully expanded condition, with the wire elements 105 expanding radially outwardly and bearing against the interior surfaces of the artery 155 to secure the anchor device 10 in position at the target site 160. The radial expansive forces of the anchor stent 100 provide ample resistance to withdrawal of the anchor device 10, thereby accommodating the introduction of a larger catheter 170 that may be used for providing treatment at target site 160 as described below.

In some medical cases, such as for stroke thrombectomy, the anchor device 10 may be useful for guiding larger catheters 170 through tortuous vessel 155 while minimizing insertion forces and potential trauma. In such embodiments, a tri-axial catheter system 180 in conjunction with the anchor device 10 may allow for the rapid catheterization of the distal cervical internal carotid artery and vertebral artery required during emergency stroke thrombectomy cases for patients with difficult tortuous vascular vessel 155. With reference to FIG. 2, the following describes an example procedure for using the anchor device 10 with the tri-axial catheter system 180.

The anchor stent 100 is first introduced to the target site 160 via the guidewire 135 and the microcatheter 165 in a similar fashion as described previously. Once the anchor stent 100 is in position at or near the target site 160, a second catheter 175 (such as a 5-F catheter) having a larger diameter than the microcatheter 165 is introduced and advanced toward the target site 160. The second catheter 175 fits over/around the microcatheter 165 and the guidewire 135, and is guided to the target site 160 via the microcatheter 165 and the guidewire 135. Finally, the larger catheter 170, which may be 7-8 F balloon-tip guiding catheter is advanced to its desired vascular position over the previously-advanced catheters 165, 175 and the guidewire 135. Once the larger catheter 170 is in position at the target site 160, the anchor device 10 may be removed. In some embodiments, the anchor device 10 may be resheathed by holding the anchor device 10 stationery while advancing the 2.8 F microcatheter 135 over the anchor device 10. As the microcatheter 135 is advanced over the anchor device 10, the anchor device 10 partially or entirely collapses into the microcatheter 135. Thereafter, both the microcatheter 135 (with the anchor device 10) and the second catheter 175 are removed, leaving the larger catheter 170 in position at the target site 160 to allow the thrombectomy procedure to move forward.

FIG. 3 illustrates another example for employing the anchor device 10, such as for cases where it may be difficult to advance a standard 5-F catheter (such as catheter 175 of FIG. 2) into the internal carotid or vertebral artery due to markedly tortuous vascular anatomy 185 in an elderly and/or hypertensive patient. With reference to FIG. 3, the innominate artery, origin of the left common carotid, or origin of the left subclavian artery may be more easily and rapidly catheterized by introducing the anchor device 10 (in a similar fashion as described with reference to FIG. 2) with a stiffer 6-F to 7-F distal hook-shaped, coronary-style guiding catheter 190. In one example process, the guiding catheter 190 is advanced through the artery 185 to a target site (not shown). Thereafter, a suppler microcatheter 195, such as a 2.3-F to 2.8-F microcatheter having an inner diameter ranging between 0.021 in. to 0.027 in., is then advanced coaxially through the guiding catheter 190 and into the distal target cervical artery 185 (or other vessel) over a guidewire 200. Due to its small size, the microcatheter 200 may have a better chance of rapidly navigating tortuous vascular anatomy while not dislodging the 6-7 F proximal guiding catheter 190. Once the microcatheter 195 has been advanced to the cervical-petrous junction of the ICA or the distal cervical vertebral artery, the guidewire 200 may be removed and replaced with the anchor device 10 in a similar process as described with reference to FIG. 2.

In some embodiments, a miniaturized version of the anchor device 10 as described with reference to FIGS. 1-3 may allow safer and more rapid intracranial catheter exchanges. This advantage may be due to greater stability of the distal exchange wire and much lower risk of potentially fatal intracranial artery perforations. Such an anchor device 10 may be useful in coronary artery catheter exchanges and interventions. In other embodiments, a larger version of the anchor device 10 may be useful for catheter exchanges in larger caliber vessels, such as the pulmonary artery, aorta (especially during stent-grafting of abdominal and thoracic aneurysms), and the inferior and superior vena cavae. In still other embodiments, the anchor device 10 may also be useful in non-vascular endoscopic catheter interventions such as those within the biliary tree, GI tract, urinary system, and tracheobronchial tree.

FIG. 4 illustrates another embodiment of the anchor stent 100 with a porous barrier 205 that provides a flow passage for blood and other substances to allow the anchor device 10 to also function as a filter, such as an inferior vena cava (IVC) filter. With reference to FIG. 4, the anchor stent 100 may include a plurality of connector struts 210 that coalesce to form a closed, conical shape at the distal end 150 of the anchor stent 100. The porous barrier 205, which may be formed of a thin layer 215 of graft material (such as polyurethane or other suitable polymer), surrounds the distal end 150 of the anchor stent 100. The barrier 205 includes a plurality of perforations or pores 220 which may be of any suitable diameter to filter particles of a desired size. In some embodiments, the pores/perforations 220 may range in diameter from 75 microns to 125 microns. In use, the anchor stent 100 is advanced and positioned at a target site in a similar fashion as described with reference to FIGS. 1-3. The porous barrier 205 is positioned to accommodate blood flow through the inferior vena cava, but otherwise traps thromboemboli from the pelvis and/or lower extremities that could otherwise cause a fatal pulmonary embolus if it reached the lungs.

Figure 5:
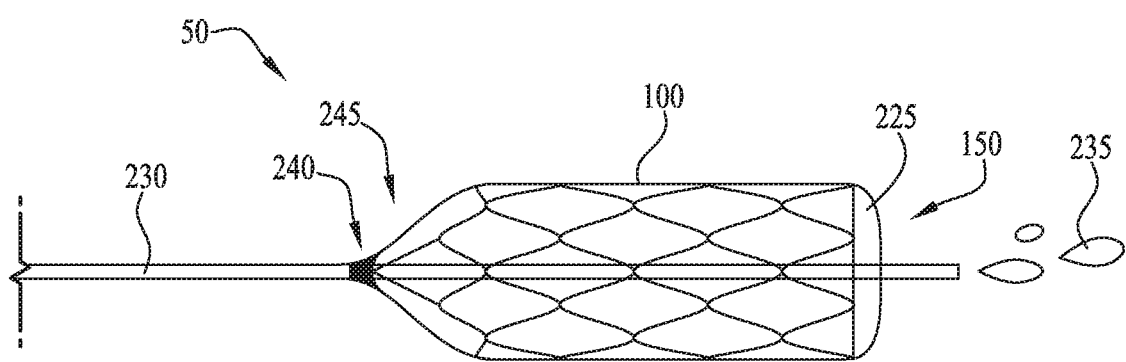
FIG. 5 illustrates another embodiment of an anchor stent with a distal end fitted with a nonporous barrier.

FIG. 5 illustrates another embodiment of an anchor device 50 that may be used an embolic device, where the anchor stent 100 may be detachable, or as an antegrade flow occluder to provide a mechanism for infusing therapeutic particles and/or substances to a target site (not shown) at which the anchor device 50 is deployed. With reference to FIG. 5, the distal end 150 of the anchor stent 100 includes a cap 225 that may be made of polyurethane or other suitable polymer. Preferably, the cap 225 is nonporous, but in some embodiments, the cap 225 may be porous similar to the porous barrier 205 described with reference to FIG. 4. Instead of a guidewire (such as guidewire 135 in FIG. 1), the anchor device 50 includes a flexible hypotube 230 that runs through the stent and extends outwardly from the cap 225 at the distal end 150. The flexible hypotube 230 accommodates the injection of liquid embolic agents 235, such as n-Butyl cyanoacrylate (NBCA), onyx, or other suitable substances/particles for delivery to the target site.

In some embodiments, the anchor device 50 may also include a detachment zone 240 adjacent the proximal end 245 of the anchor stent 100. By detaching the anchor stent 100 at the detachment zone 240, the anchor stent 100 itself (i.e., without the hypotube 230) may be left in the vessel permanently, if desired. In other embodiments, to avoid or minimize potential backflow of the injected agents 235, particularly backflow of larger particles, the proximal end 245 of the anchor stent 100 may include a porous barrier (not shown) similar to porous barrier 205 of FIG. 4 to trap the injected agents 235.

FIG. 6 illustrates another embodiment of an anchor device 60 that may ease the advancement of larger catheters up tortuous, atherosclerotic brachiocephalic vessels, especially in older patients, and particularly during endovascular clot retrieval in acute strokes and during carotid stenting procedures. With reference to FIG. 6, the anchor device 60 includes a plurality of wire elements 605 coupled together to form an anchor stent 600, which is a generally tubular-shaped, self-expanding mesh structure. Similar to the anchor stent 100 of FIG. 1, the wire elements 605 may be coupled together, such as via a welding process, to create a "closed-cell" design with sufficient rigidity to allow the anchor stent 600 to move through tortuous vessels 640, as further described with reference to FIGS. 7 and 8.

The anchor stent 600 includes a first stent segment 610 adjacent a proximal end 615, and a second stent segment 620 adjacent a distal end 625, the first and second stent segments 610, 620 connected to one another via a transition portion 630 to form a continuous anchor stent 600 of varying diameter. As illustrated in FIG. 6, the first stent segment 610 is longer and narrower as compared to the second stent segment 620. For example, in one embodiment, the length $L_{NS}$ may range between 10 cm and 30 cm, while the length $L_{WS}$ may range between 2 cm and 4 cm. In addition, the diameter $D_{NS}$ of the first stent segment 610 may be approximately one-half of the diameter $D_{WS}$ of the second stent segment 620. For example, the diameter $D_{NS}$ may be approximately 3 mm, while the diameter $D_{WS}$ may be between 6 mm and 7 mm, with the transition portion 630 gradually tapering/increasing between the end of the first stent segment 610 and the beginning of the second stent segment 620. It should be understood that in other embodiments, other suitable diameters for $D_{NS}$ and $D_{WS}$ and suitable lengths for $L_{NS}$ and $L_{WS}$ may be used without departing from the principles of the disclosed subject matter.

FIGS. 7 and 8 illustrate example embodiments for employing the anchor device 600 to advance a large catheter 640 (e.g., an 8 F eV3 Cello or 8 F Cook Shuttle catheter) through tortuous vessels 645. With reference to FIGS. 7 and 8, the anchor stent 600 and guidewire 635 are advanced through the vessel 645 (in a similar fashion as described previously with reference to the anchor device 10 of FIGS. 1-3) until the wider stent segment 620 reaches a target site 650. At the target site 650, the wider stent segment 620 is in a fully expanded condition, with the wire elements 605 expanding radially outwardly and bearing against the interior surfaces of the vessel 645 to secure the anchor stent 600 in position at the target site 650. Thereafter, the catheter 640 is advanced over the guidewire 635 and the longer, narrow stent segment 610 toward the target site 650. As the catheter 640 advances over the narrow stent segment 610, the narrow stent segment 610 collapses inside the catheter 640. As illustrated in FIG. 8, the longer, narrow stent segment 610 portion (with a stent design that promotes axial force transmission) maintains the catheter 640 generally centered within the vessel 645 and away from the vessel interior wall, thereby simplify the catheterization process. In this manner, the longer, narrow stent segment 610 obviates the need for a central catheter or dilator for the delivery of the large catheter 640.

It is intended that subject matter disclosed in any one portion herein can be combined with the subject matter of one or more other portions herein as long as such combinations are not mutually exclusive or inoperable. In addition, many variations, enhancements and modifications of the concepts described herein are possible.

The terms and descriptions used above are set forth by way of illustration only and are not meant as limitations. Those skilled in the art will recognize that many variations can be made to the details of the above-described embodiments without departing from the underlying principles of the invention.

The invention claimed is:

1. A method for filtering particles in a body lumen of a patient, the method comprising:
   inserting a first catheter comprising a first diameter into the body lumen;
   advancing a distal end of the first catheter to a target site in the body lumen;
   inserting an anchor-filter device in a collapsed state through the first catheter, the anchor-filter device comprising:
   a guide member;
   a self-expanding anchor stent comprising self-expanding wire elements attached to a distal end of the guide member; and
   a filter layer comprising a porous barrier attached to a distal end of the self-expanding anchor stent opposite the guide member;
   advancing the self-expanding anchor stent through the distal end of the first catheter to allow the self-expanding wire elements to expand the anchor stent and apply a radial force to an interior wall of the body lumen to anchor the guide member at the target site;
   inserting a second catheter comprising a second diameter greater than the first diameter into the body lumen;
   advancing a distal end of the second catheter over the guide member toward the target site; and
   filtering particles within the body lumen using the anchor-filter device.

2. The method of claim 1, further comprising using the second catheter to perform a thrombectomy procedure.

3. The method of claim 2, further comprising removing a thrombus and the particles from the body lumen with the second catheter and the anchor-filter device.

4. The method of claim 1, further comprising using the second catheter to perform a stenting procedure.

5. The method of claim 1, wherein the stenting procedure comprises carotid stenting.

6. The method of claim 1, wherein to anchor the guide member at the target site, the method further comprises anchoring the guide member within the body lumen selected from a group comprising an intracranial artery or vein, a carotid artery, vertebral artery, a coronary artery or vein, a pulmonary artery, an aorta, an inferior or superior vena cava, a biliary tree, a gastrointestinal (GI) tract, a ureter, and a tracheobronchial tree.

7. The method of claim 1, wherein the porous barrier comprises a graft material.

8. The method of claim 7, wherein the graft material comprises a polyurethane or other polymer.

9. The method of claim 1, wherein guide member comprises a guidewire.

10. The method of claim 9, wherein the anchor stent further comprises a plurality of connector struts coalescing to form a strut tip opposite the filter layer, the strut tip attached to the guidewire.

11. The method of claim 1, wherein the anchor stent further comprises:
    a first expandable stent segment having a first expanded width; and
    a second expandable stent segment having a second expanded width different from the first expanded width.

12. The method of claim 11, wherein the anchor stent further comprises a transition portion that gradually tapers between the first expanded width and the second expanded width.

* * * * *